(12) United States Patent
Hautala et al.

(10) Patent No.: US 6,687,535 B2
(45) Date of Patent: Feb. 3, 2004

(54) CONTROLLING OF FITNESS EXERCISE

(75) Inventors: Arto Hautala, Oulu (FI); Ilkka Heikkilä, Oulu (FI); Timo Mäkikallio, Oulu (FI); Seppo Nissilä, Oulu (FI); Mikko Tulppo, Oulu (FI)

(73) Assignee: Polar Electro Oy, Kempele (FI)

( * ) Notice: Subject to any disclaimer, the term of this patent is extended or adjusted under 35 U.S.C. 154(b) by 151 days.

(21) Appl. No.: 09/792,302

(22) Filed: Feb. 23, 2001

(65) Prior Publication Data

US 2001/0027266 A1 Oct. 4, 2001

(30) Foreign Application Priority Data

Feb. 23, 2000 (FI) .............................. 20000418

(51) Int. Cl.[7] .......................................... A61B 5/0468
(52) U.S. Cl. ........................................ 600/520; 482/9
(58) Field of Search ....................... 482/8, 9; 600/382, 600/384, 390, 481, 408, 509, 520

(56) References Cited

U.S. PATENT DOCUMENTS

| | | | |
|---|---|---|---|
| 4,566,461 A | | 1/1986 | Lubell et al. |
| 5,598,849 A | * | 2/1997 | Browne ..................... 128/707 |
| 5,738,612 A | | 4/1998 | Tsuda |
| 5,782,772 A | * | 7/1998 | Stegmann .................. 600/520 |
| 5,853,351 A | * | 12/1998 | Maruo et al. .................. 482/8 |
| 5,891,044 A | * | 4/1999 | Golosarsky et al. ........ 600/509 |
| 5,921,940 A | * | 7/1999 | Verrier et al. ............... 600/518 |
| 6,176,241 B1 | * | 1/2001 | Blau et al. .................. 128/898 |
| 6,212,427 B1 | * | 4/2001 | Hoover ........................ 600/515 |
| 6,411,841 B2 | * | 6/2002 | Heikkila ...................... 600/513 |

FOREIGN PATENT DOCUMENTS

| | | |
|---|---|---|
| EP | 0 556 702 A3 | 8/1993 |
| FI | WO 96/20640 | 7/1996 |
| FI | 100452 B | 12/1997 |

OTHER PUBLICATIONS

Ringwood, J.V., "Anaerobic Threshold Measurement Using Dynamic Neural Network Models," *Computers in Biology and Medicine*, Jul. 1999, Elsevier, UK (abstract).

* cited by examiner

Primary Examiner—Jeffrey R. Jastrzab
Assistant Examiner—Frances P. Oropeza
(74) Attorney, Agent, or Firm—Hoffman & Baron, LLP

(57) ABSTRACT

A heart rate measuring arrangement for controlling a recovery exercise of a person from a fitness exercise which measures the heart rate, forms control information, and displays the formed control information so that the recovery exercise is performed at a controlled heart rate level.

53 Claims, 8 Drawing Sheets

CONTROLLING OF FITNESS EXERCISE

BACKGROUND OF THE INVENTION

1. Field of the Invention

Figure 1:
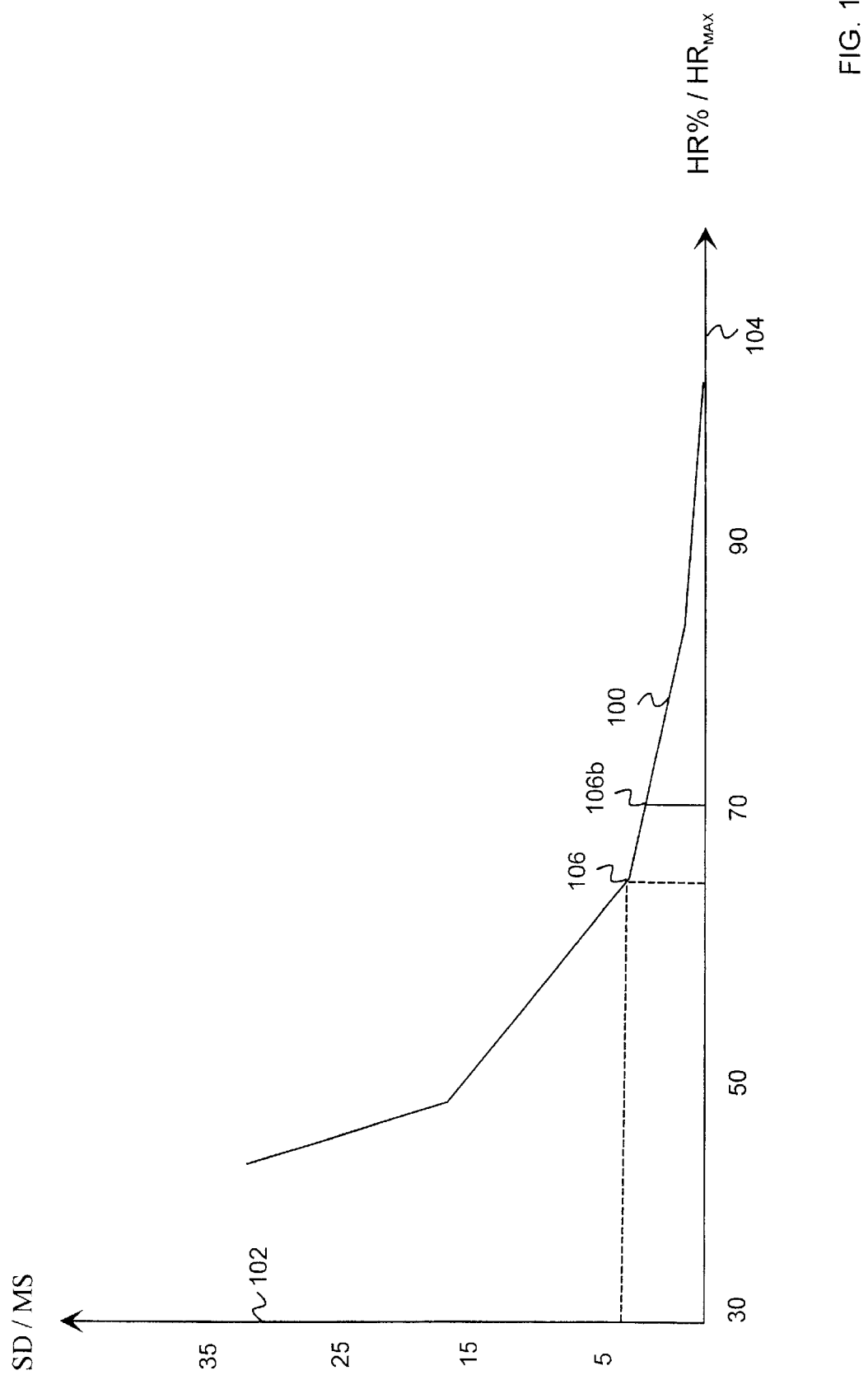

The invention relates to exercise and sports, particularly to applications in which recovery of a person from a fitness exercise performed by him/her is controlled.

2. Brief Description of the Related Art

Recovery after exercising is important both to metabolism and muscle care. Stress pain resulting from exercising can be reduced considerably by a well-performed recovery exercise. In that case recovery is achieved in shorter time and the capability of the muscles and the system to perform the next exercise improves considerably. The most important function of the recovery exercise is to remove any lactic acid, i.e. lactate, accumulated in the body quickly and efficiently so that the lactate does not cause pain and post-exercise stress in the muscles. For this reason, the recovery exercise has to be performed at a stress level which prevents build-up of additional lactate, but enables effective removal of lactate from the body. Thus the recovery exercise is performed below the anaerobic threshold.

Nowadays various instructions and rules are used in sports coaching and training to keep recovery exercise at a certain adequate level for a predetermined time. For example, the exercising person may be told to recover from exercising by walking for 10 minutes or by keeping the heart rate at 120 beats/minute for 10 minutes.

The prior art method of recovering from a fitness exercise has considerable disadvantages. It is clear that the above-mentioned instructions are very general and by no means optimal for achieving as efficient recovery as possible. The above-mentioned instructions take the characteristics of an exerciser into account only indirectly, e.g. a coach may give different instructions for performing recovery exercise to athletes with different fitness levels.

SUMMARY OF THE INVENTION

The object of the invention is to provide an improved method of controlling a fitness exercise. This is achieved with the method to be described in the following. The method concerns controlling recovery of a person from a fitness exercised performed by him/her. The method comprises controlling a recovery exercise following the fitness exercise so that it is performed at a heart rate level below the threshold value of heart rate, heart rate variation being higher than a preset threshold value of heart rate variation at heart rate levels lower than the-threshold value of heart rate.

The invention also relates to a heart rate measuring arrangement. The heart rate measuring arrangement comprises measuring means for obtaining heart rate information, forming means for forming control information from the heart rate information obtained by measuring to control the recovery exercise, display means for presenting the formed control information.

The preferred embodiments of the invention are disclosed in the dependent claims.

The invention relates to a method and apparatus for controlling recovery of a person from a fitness exercise performed by him/her. In this description the fitness exercise refers to a physical exercise which is at least partly performed at a workload level exceeding the anaerobic level, in which case lactate is accumulated in the muscles of the person's body. The recovery exercise means the exercise phase that follows the actual fitness exercise or competitive exercise which is mainly performed at a workload level below the anaerobic level. Controlling means control information provided e.g. by a heart rate monitor, such as the heart rate level, the heart rate limits within which the recovery exercise should be performed, and the time preferably used for the recovery exercise.

In a preferred embodiment of the invention, an anaerobic threshold value, i.e. the threshold value of heart rate, is found on the basis of changes in heart rate variation. Here heart rate variation means temporal variations in heart beats around the expected moments at which the heart should beat. In a preferred embodiment, the variation is calculated as moving standard deviation, but it, can also be calculated by another prior art mathematical method, e.g. by a method which utilizes the distribution function between the heart rate and the heart rate variation. As a function of heart rate, the heart rate variation naturally decreases as the heart rate, i.e. the heart beat frequency, increases. FIG. 1 illustrates variation as a function 100 of heart rate, i.e. the x axis 104 shows the heart rate as per cent of the maximum heart rate and the y axis 102 shows standard deviation as milliseconds around the expected moment at which the heart should beat. FIG. 1 illustrates dependency between the heart rate variation and the heart rate, which applies to the majority of people. When the heart rate level is e.g. 40% of the maximum heart rate, the heart rate variation is between 15 to 25 milliseconds. The maximum heart rate means the heart rate value that can be calculated e.g. by the formula (220–age), in which case the maximum heart rate of a 40-year old person is 180. The maximum heart rate can also be measured at the maximal workload or determined from the person's physiological properties using a neural network, for instance. It can be seen from FIG. 1 that as the heart rate level approaches the maximum heart rate, the heart rate variation decreases considerably. The angular point of heart rate variation, i.e. the change point 106, is achieved at a heart rate level which is usually about 62 to 65% of the maximum heart rate, but may also vary in a wider range, e.g. 55 to 70% of the maximum heart rate. The change point 106 of heart rate variation is connected to the anaerobic limit point 106b of energy metabolism. It can be seen from FIG. 1 that the anaerobic limit point 106b is at a slightly higher heart rate level, i.e. 15 to 25 beats higher, than the change point 106 of heart rate variation. At heart rate levels above the anaerobic limit point 106b exercise is anaerobic, whereas at heart rate levels below the limit point exercise is aerobic. The intersection point of the change point 106 is about 4 milliseconds at the y axis, but may vary e.g. from 3 to 5 milliseconds.

In this description the fitness exercise refers to a physical exercise which is at least partly performed at a workload level exceeding the anaerobic limit, in which case lactate accumulates in the muscles of the person's body. Lactate concentration can be estimated for a given period, e.g. a few hours before and after the fitness exercise, and thus the invention is not limited to the actual performance of the fitness exercise. A fitness exercise can be divided e.g. into the following phases: warm-up, active phase, recovery phase, in which case the fitness exercise is preceded and followed by a rest. Different phases can be defined and distinguished from one another e.g. on the basis of heart rate levels and/or workload levels. Then the recovery phase, for example, can be defined as an exercise level where the heart rate level drops from 130 beats/minute to a rest level of 70 beats/minute. The recovery phase is considered to begin when the heart rate level is below the limit of the active phase, i.e. 130 beats/minute, for two minutes, for instance.

In a preferred embodiment of the invention the exercising person monitors his/her heart rate at least at the end of the fitness exercise. At the beginning of the recovery exercise, the exerciser starts to walk, for example, so that the heart rate drops to a heart rate value below the change point of heart rate variation. For the recovery to be maximally efficient, it should be performed as close to the change point as possible, i.e. at a heart rate which is about 55 to 60% of the maximum heart rate.

In another preferred embodiment of the invention, the physical condition of the exercising person is also taken into account in the calculation of the change point of heart rate variation. Physical condition can be defined e.g. as the maximal oxygen uptake, which can be determined e.g. by measuring the maximal oxygen uptake at the maximal workload or by forming an estimate by means of a neural network, into which one or more physiological parameters are fed as input parameters and/or several stress parameters that describe the workload. The physical condition affects curve 100 shown in FIG. 1 so that the change point of heart rate variation of a fit person is at a higher heart rate level than that of an unfit person. However, the proportional share of heart rate variation of the maximum heart rate is the same for both these persons. Thus a fit person can exercise at a higher workload without the exercise being anaerobic. The distance between the points 106 and 106b depends on the person's condition and lactate properties. In the case of a person with a very good condition, for example, the distance between the points is larger, which is taken into account in an embodiment by considering the person's condition in calculation and determination of controlling. In determination of point 106b a prior art lactate tolerance test, for example, is used. In the test, blood tests are used to locate the threshold of the angular coefficient of the lactate curve under stress, which corresponds to the heart rate level at point 106b.

In a preferred embodiment recovery from a fitness exercise is controlled by means of the vanishing point of heart rate variation and the lactate that has accumulated in the body during exercise. According to an embodiment, the amount of lactate in the body is estimated by a two-part mathematical model which is described in greater detail in FIG. 2. In this specification the mathematical model refers to a set of mathematical operations and rules for determining output parameter values from the input parameter values. Mathematical operations include arithmetic operations, such as addition, subtraction and multiplication. The mathematical model can naturally be implemented as a table or a database, in which case the output parameter value corresponding to a given input parameter is read directly from the database. It is clear that the model may consist of only one part or of more than two parts. One or more parameters 202 representing the person's heart rate, such as the average heart rate, standard deviation of the heart rate or the like, are fed into the first part 200 of the model as input parameters. The input data of the model also comprise one or more stress parameters 204 describing the exercise workload, such as running speed or pedalling speed of the exercise bike. The third set of input parameters for the model consists of one or more physiological parameters 206 of the person, such as height, weight or gender. The above-mentioned input parameter sets 204 to 206 are optional, i.e. they may be included in the model separately, simultaneously, or be omitted from the model. In an embodiment of the invention the first part 200 of the model is implemented as a neural network which has been trained with user data comprising information on hundreds or even thousands of users. In an embodiment of the invention, the first part of the model provides the person's stress level 208 during exercise as the output. The output parameter set 210 provided by the model represents one or more fitness parameters which describe the person's physical condition, such as the maximal oxygen uptake or the fitness index.

The input parameters to be fed into the second part 212 of the model include the above-mentioned information representing the exercise stress level 208 and optionally one or two fitness parameters 210 describing the user's condition. In a preferred embodiment of the invention, the second sub-model 212 is a mathematically formed physiological model which gives the amount 214 of lactate in the person's body as the output parameter on the basis of the input parameters. The amount 214 of lactate is used as the input parameter of control routines 216 which control removal of lactate from the body, using the control output 218 for monitoring that the duration and efficiency of the recovery exercise are sufficient.

In the solution of the invention for controlling a recovery exercise, the person whose recovery is to be monitored, preferably uses a heart rate monitor. The heart rate monitor is a device employed in sports and medicine, which measures human heart rate information either from an electrical impulse transmitted by the heart or from the pressure produced by the heart beat on an artery. Generally, the heart rate monitors comprise an electrode belt to be fitted around the user's chest to measure the heart rate by means of two or more electrodes. The electrode belt transmits the measured heart rate information inductively as one or more magnetic pulses per heart beat, for instance, to a wrist-worn receiver unit. On the basis of the received magnetic pulses, the receiver unit calculates the heart rate and, when needed, other heart rate variables, such as moving standard deviation of the heart rate. Often, the receiver unit, i.e. the wrist monitor, also comprises a display for showing the heart rate information to the exerciser and a user interface for the use of other facilities of the heart rate monitor. In the above-described situation, the heart rate monitor refers to the entity consisting of the electrode belt and the receiver unit. The heart rate monitor can also be a one-piece device in which the display means are located on the chest, and thus there is no need to transmit the information to a separate receiver unit. Further, the structure of the heart rate monitor can be such that it only comprises a wrist-worn monitor which operates without the electrode belt to be fitted around the chest, measuring the heart rate information from the vessel pressure. In the description of the invention, the heart rate measuring arrangement refers to the above-described heart rate monitor solutions. The heart rate measuring arrangement also comprises solutions in which heart rate information is transmitted to an external computer or to a data network, which has display means, such as a computer screen, for presenting the information measured or generated by the heart rate monitor.

In a preferred embodiment of the invention, the functions required by the method of the invention are performed in the receiving unit if the heart rate monitor consists of two pieces. One or more mathematical models of the invention and other functions required by the model are preferably implemented by software for a general-purpose processor. The models and functions can also be implemented as ASIC, with separate logic components or in a corresponding manner. In a preferred embodiment of the invention, the heart rate monitor comprises means for feeding user-specific physiological information, stress information and information on a fitness exercise. The feeding means can be, for instance, a keypad of the heart rate monitor, display equipment that supports control, a speech controller, a telecommunications port for external control or the like. The heart rate monitor also preferably comprises means for controlling the exerciser during a recovery exercise. The controlling means can be e.g. the display of a heart rate monitor, a speech controller, a telecommunications port for transmitting information to external means, such as a computer, or the like.

An advantage of the invention is that it provides more accurate controlling of recovery from a fitness exercise than the prior art methods.

BRIEF DESCRIPTION OF THE DRAWINS

Figure 2A:
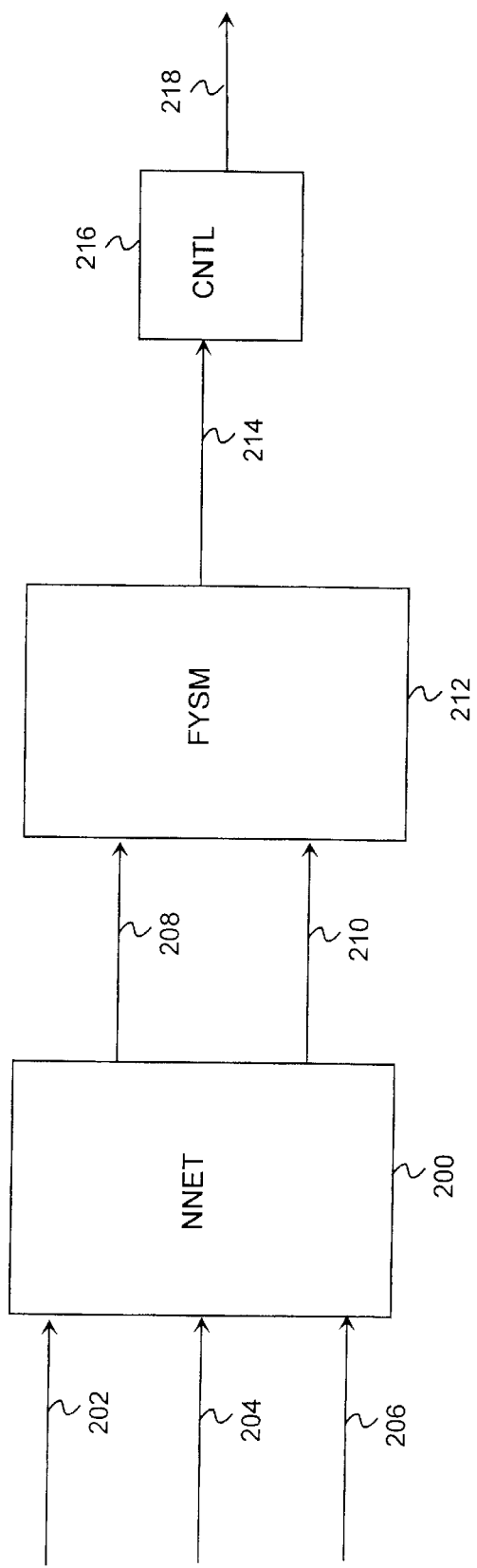
Figure 2B:
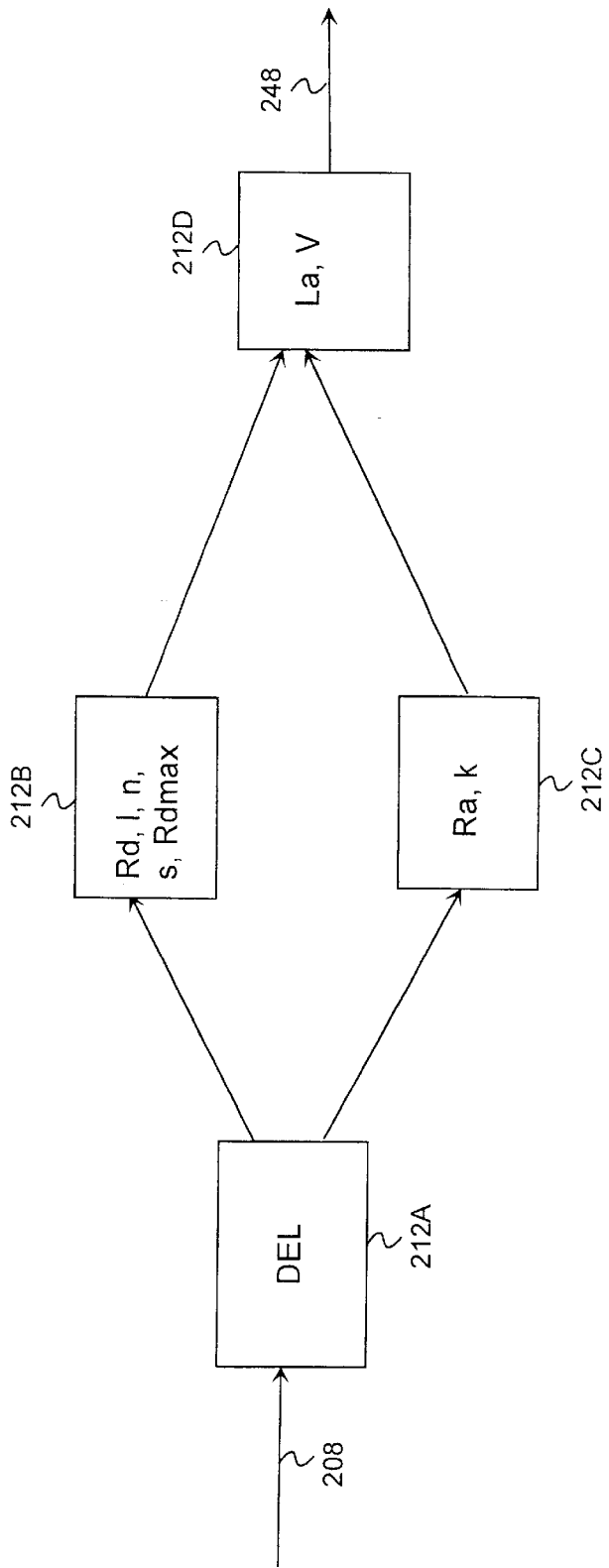
Figure 3A:
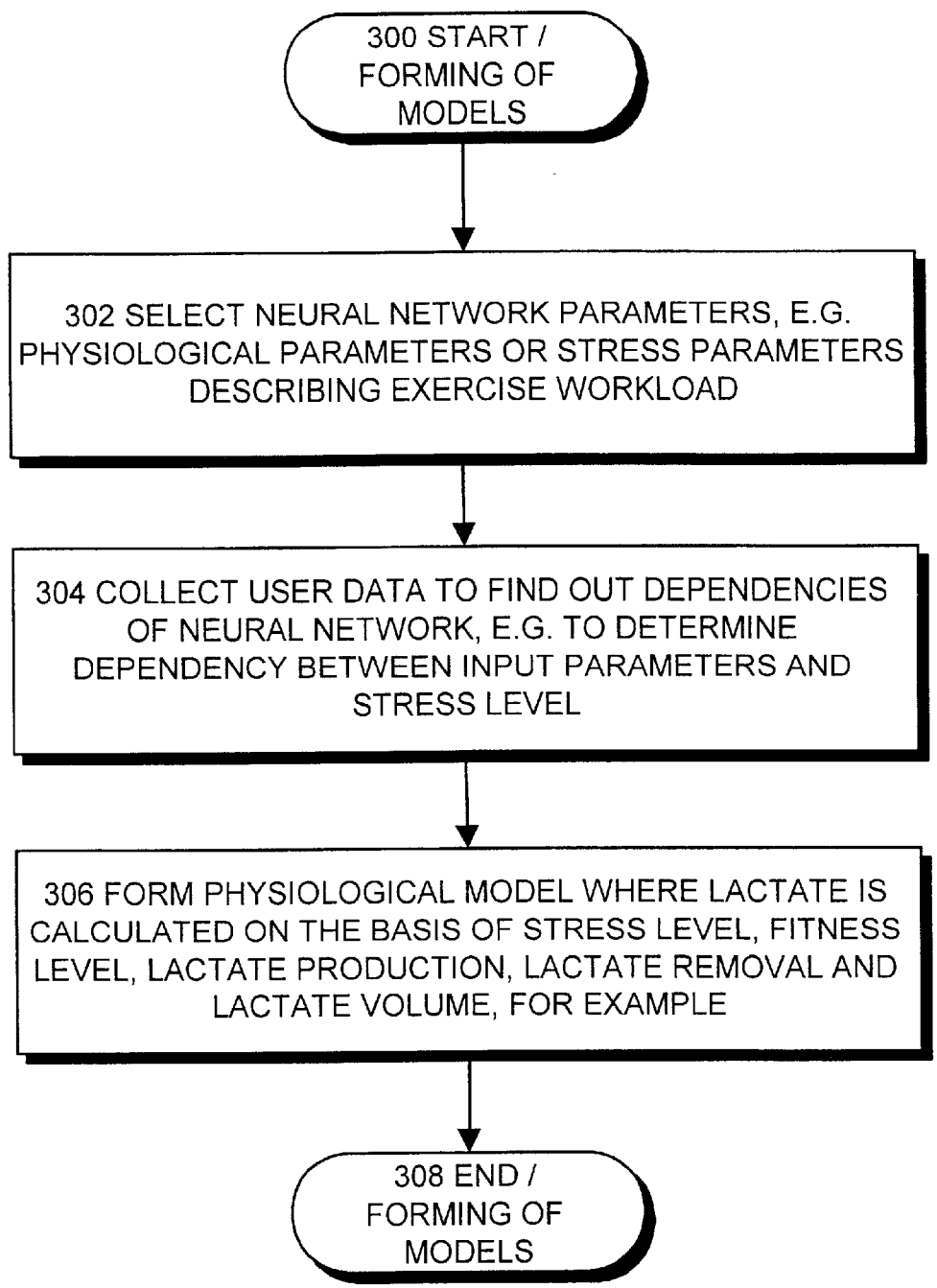
Figure 3B:
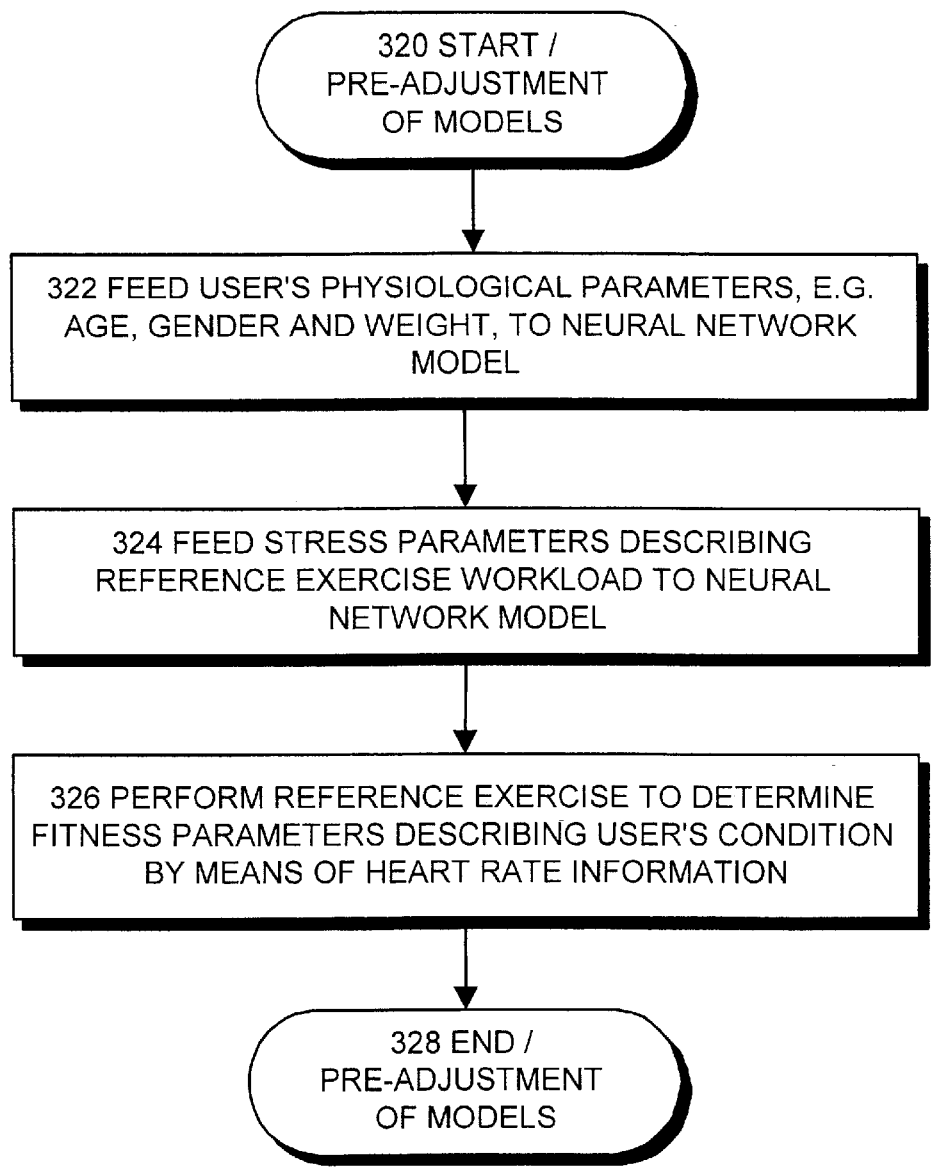
Figure 3C:
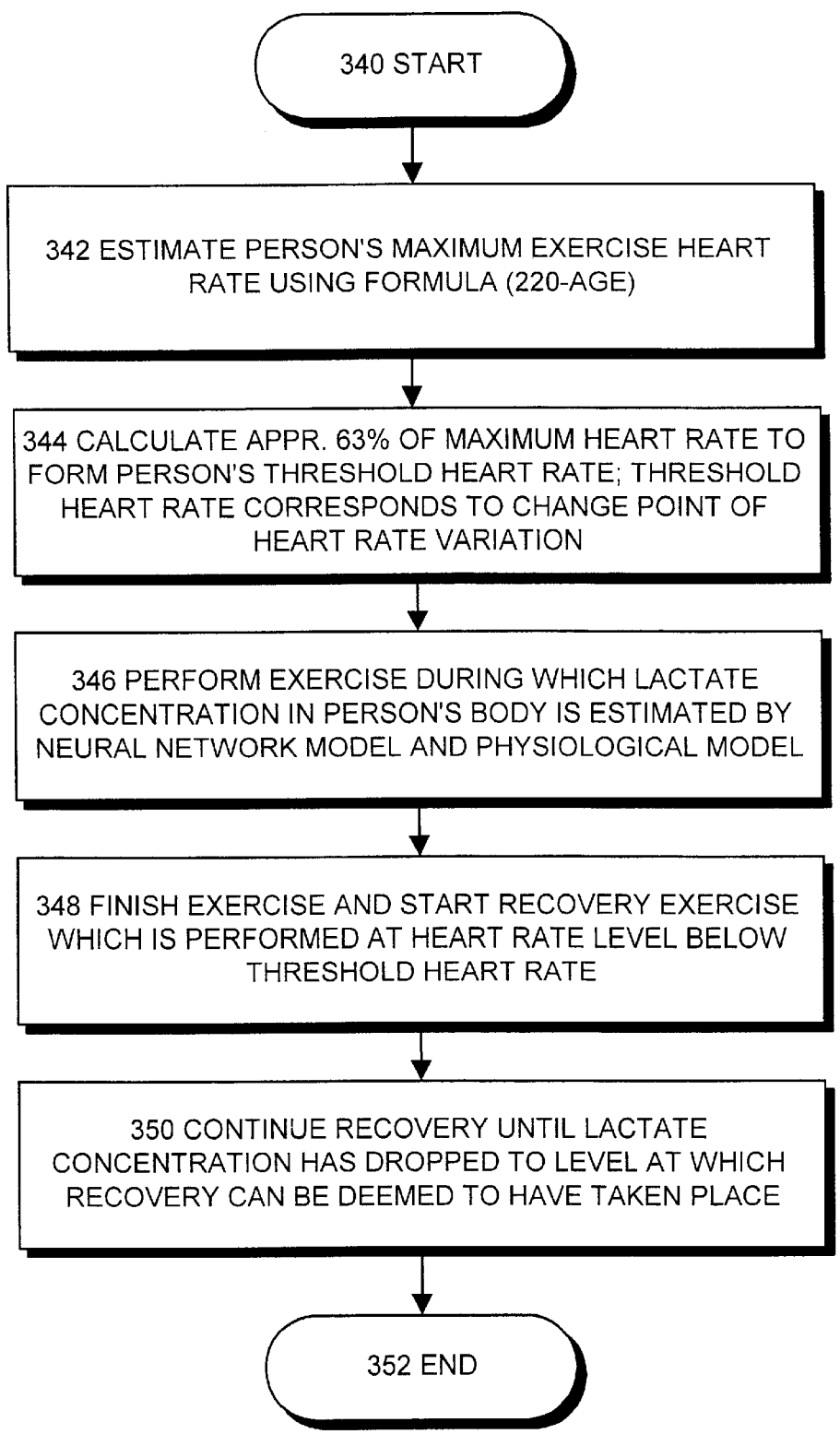
Figure 4A:
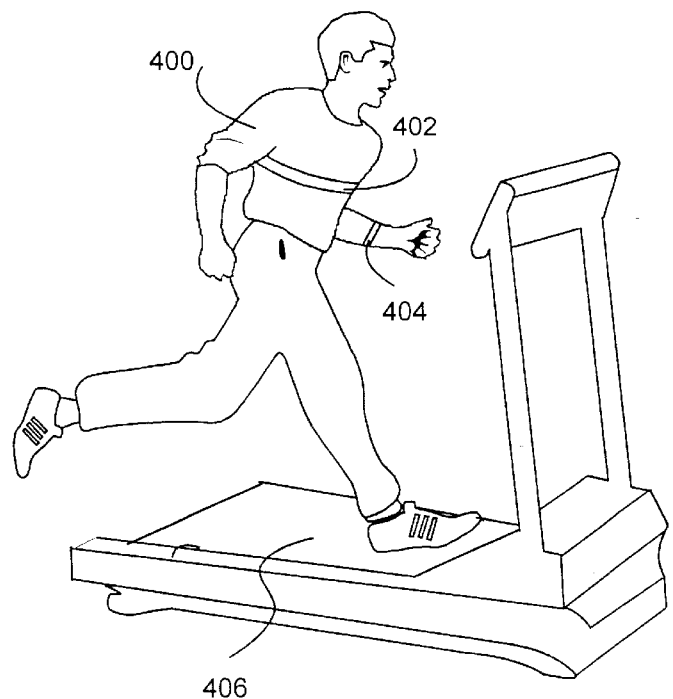
Figure 4B:
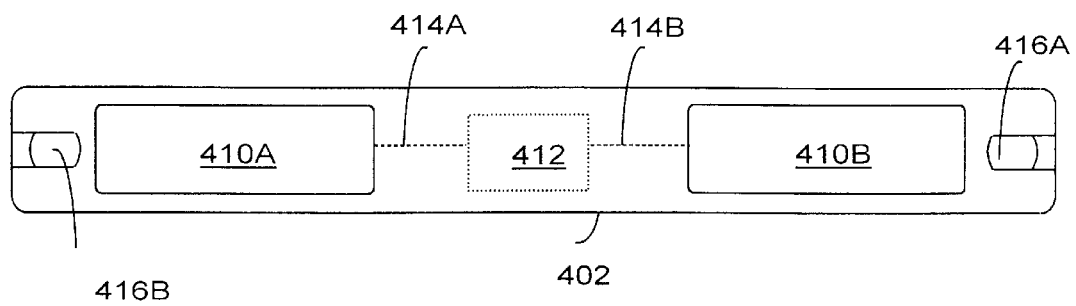
Figure 4C:
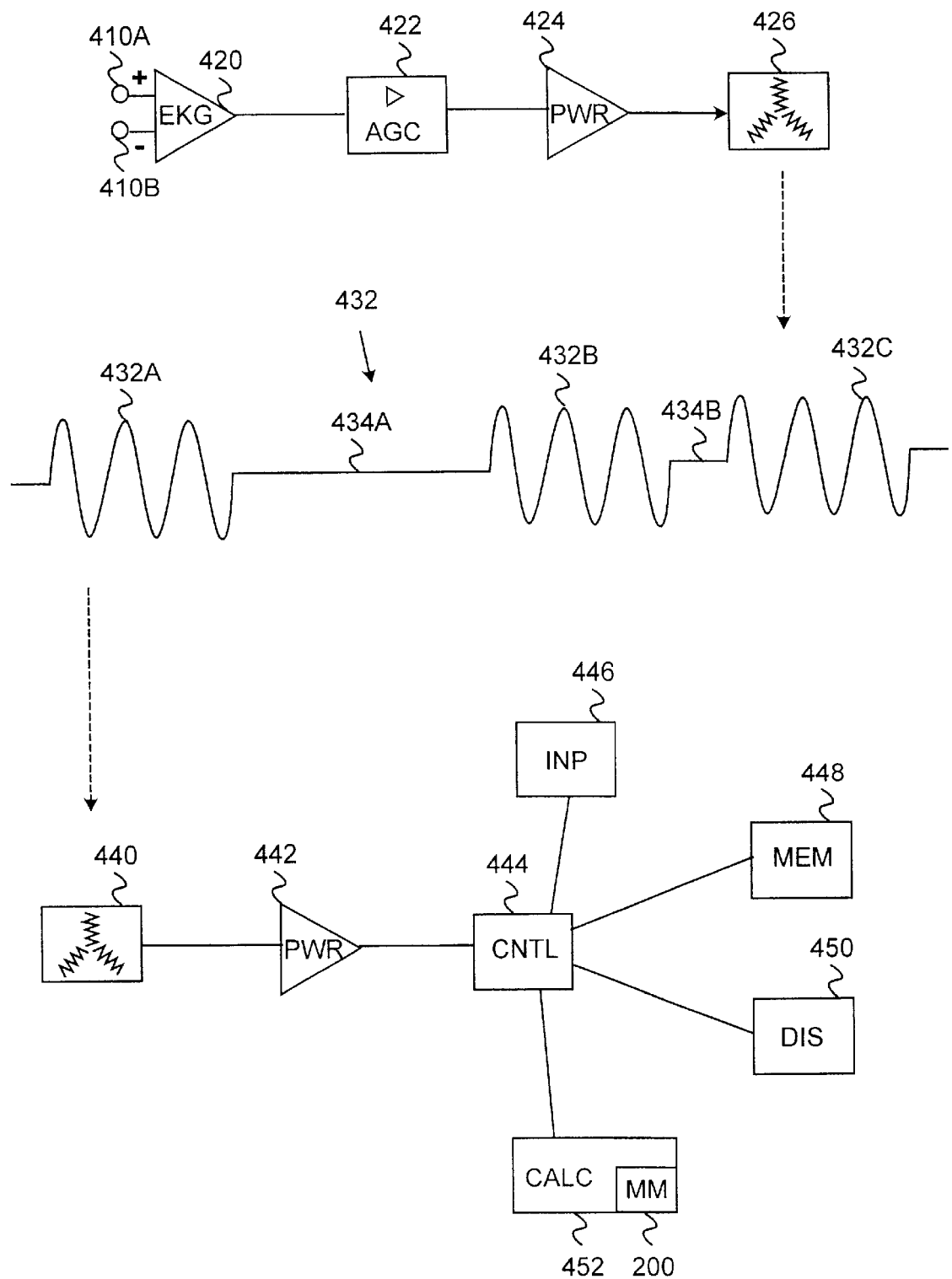

In the following, the invention will be described in greater detail with reference to the accompanying drawings, in which FIG. 1 illustrates change of heart rate variation as a function of heart rate, FIG. 2A is a block diagram illustrating a model structure according to an embodiment of the invention, FIG. 2B is a block diagram illustrating a model structure according to an embodiment of the invention, FIG. 3A is a method chart of an embodiment according to the invention, FIG. 3B is a method chart of an embodiment according to the invention, FIG. 3C is a method chart of an embodiment according to the invention, FIG. 4A illustrates an embodiment of the heart rate measuring arrangement according to the invention, FIG. 4B illustrates the electrode belt shown in FIG. 4A from the side to be fitted against the body of the person to be measured, FIG. 4C illustrates an embodiment of a two-piece heart rate monitor.

DETAILED DESCRIPTION OF THE PREFERRED EMBODIMENTS

In the following, the invention will be described by means of preferred embodiments with reference to FIGS. 1 to 4C. In an embodiment, the change point of heart rate variation, which can be determined from the maximum heart rate of a person, is used for controlling recovery. At heart rate values exceeding the change point the heart rate variation drops below the threshold value of heart rate variation. The majority of people have a threshold value of 4 ms. When the fitness exercise is finished or the workload is reduced, the heart rate starts to decrease and thus the heart rate variation begins to increase. When the variation exceeds the threshold value, recovery can be deemed to have begun. Heart rate variation can be utilized for controlling the recovery exercise e.g. so that a 10-minute recovery exercise is performed at a workload which keeps the heart rate variation between 6 to 8 ms. Naturally the heart rate can also be employed for controlling recovery because the heart rate and the heart rate variation correlate with each other.

FIGS. 3A to 3C illustrate a preferred embodiment of the method according to the invention. A neural network 200, which is shown in FIG. 2, is formed in steps 302 to 304 of FIG. 3A. The invention is not limited to the use of a neural network as the model for determining the stress level on the basis of the heart rate information, but some other prior art classifier can also be used. In step 302 parameters are selected for the model. The parameters that describe the person's heart rate information are compulsory, whereas physiological parameters and stress parameters are optional. Parameters that represent the heart rate information include the heart rate, standard deviation of the heart rate, change rate of the heart rate and similar parameters that can be calculated from the heart rate. According to an embodiment, only the heart rate is used in the model, but the above-mentioned heart rate parameters can be combined in various ways as the input parameters of the model. Physiological parameters are optional input parameters of the model. One or more physiological parameters, such as the person's age, gender, height, weight and the like can be inserted into the model. Furthermore, the input parameters of the model may comprise one or more stress parameters that describe the exercise workload. The stress parameters typically comprise e.g. running speed, pedalling speed of the exercise bike or a similar parameter. In step 304 the neural network model is trained, i.e. the weighting coefficients of the model parameters are matched. The model is preferably trained by means of a large set of users, which includes e.g. over 1000 users. The larger the number of users taken into account in training of the model and the more heterogeneous the group used in respect of its physiological properties and physical condition, the better the model parameters can be matched. In an embodiment of the invention, the model yields the person's stress level during exercise, which can be used for controlling recovery. The stress level is expressed e.g. as workload/time unit. In an embodiment the model yields one or more fitness parameters describing the person's physical condition as output parameters. The fitness parameter may be e.g. the maximal oxygen uptake or the fitness index. In a preferred embodiment the model yields the amount of lactate in the body, which is used in the controlling of recovery. The model is preferably calibrated by real user data before the actual use. In respect of lactate this means that the real amount of lactate in blood is measured a few times during an exercise, and the real measurement result is fed into the model, which calibrates the model parameters by means of feedback so that the real measured value is obtainable by the model. As a result of calibration the model yields better and more accurate estimates of the amount of lactate in blood during the actual use.

In the following, the generation and principles of a physiological model related to step 306 will be described on the basis of physiological properties of a person. The efficiency of a fitness exercise can be described as exercise intensity in relation to time. The intensity can be examined as heart beat frequency in relation to time. However, if momentary exercise intensity is examined this way, the result will be only a momentary rough estimate of the stress level, which gives hardly any information on the exercise performed. The effect of long-term exercise stress depends on the individual, i.e. a fit person sustains stress better than an unfit person. For example, both persons may be able to perform exactly the same exercise at the same intensity, but the exercise affects both persons differently: the fit person does not become significantly exhausted whereas the unfit person performs the same exercise at the extreme limits of his/her capacity. The influence of momentary stress on an individual and on the stress level experienced by the individual during exercise depends on previous stress.

In training, it is important to know the amount of cumulative stress, which increases under hard stress and decreases at rest. Concentration of lactate, i.e. lactic acid, in blood represents well the cumulative stress. The amount of lactate is the only indicator by which the cumulative stress can be measured in practice. The amount of lactate can be measured by taking a blood sample, which is analysed. This is, however, slow and requires a complex measuring arrangement. The present invention provides a non-invasive and indirect method of measuring lactate and utilizing the information on the amount of lactate in the body for controlling recovery from a fitness exercise. Referring to FIG. 2, the amount of lactate 214 is formed as a function of heart rate information 202 during the fitness exercise, and in the following recovery exercise the removal of lactate 214 from the body is monitored on the basis of the heart rate information 202.

The physiological basis for the models illustrated in FIG. 2 is obtained from human energy metabolism. Muscles receive the energy needed for exercise from ATP (adenosine triphosphate). The ATP deficiency resulting from exercise should be replenished by producing new ATP from the energy reserves. For the first 10 to 15 seconds since the exercise stress starts, creatine reserves are sufficient for producing the ATP needed by the muscles. After this, the energy obtained from the glucose in the body can be used. Fatty acids cannot be utilized until about 15 minutes after the onset of exercise stress. In short maximal stress lasting only for tens of seconds, energy production is always chiefly anaerobic. In exercise stress of a few seconds energy is produced mainly by alactic processes by means of creatine phosphate. However, the creatine phosphate reserves are small and after ten seconds of exercise stress, energy is produced mainly by lactic processes. In longer maximal stress lasting for dozens of minutes the proportion of aerobic energy production increases. However, the long-term stress employs nearly the same energy production mechanisms as the short time stress. Carbohydrates from food provide glucose which is stored in muscles as glucogen. In glucolysis glucose degrades and releases energy. The reaction may take place either aerobically or anaerobically.

Aerobic case:

glucose+$O_2$→$CO_2$+$H_2O$+energy.

Anaerobic case:

glucose→$CO_2$+$H_2O$+lactate+energy.

Lactate is thus produced in anaerobic glucolysis. The amount of lactate, i.e. lactic acid, in the body is a balance reaction. A small but equal amount of lactate is produced and removed at rest. If the workload increases, more lactate is produced, but the lactate removal mechanisms also start to function at a higher rate. If the stress level does not rise to a very high level, the lactate removal mechanisms can remove lactate at the same rate as it is produced. In hard exercise stress, more lactate is produced than removed. This leads to a rapid increase of the lactate level in the body and exhaustion. The lactate removal mechanisms of a fit person are efficient and quick to react. A lactate surplus is generated when the production rate of lactate is higher that the removal rate. A lactate curve, which presents the amount of lactate as a function of heart rate, represents in a way the person's condition. The curve of an unfit person grows more evenly than that of a fit person. The lactate level of a fit person is relatively low up to a rather high stress level. At a certain stress level, known as the lactate threshold, the curve rises steeply. This curve form can be explained by the fact that the lactate removal mechanisms of a fit person are efficient and react rapidly to the elevated production rate of lactate. The amount of lactate does not increase significantly until the maximal lactate removal rate is reached. Correspondingly, the lactate removal mechanisms of an unfit person are weaker and follow the elevated lactate production rate with a minor delay. If the lactate curve is known, it is easy to plan exercise and recovery. Exercise should take place within the lactate curve area in which development is desired because exercise generally improves blood circulation, and consequently the efficiency of the removal mechanisms. The recovery exercise, on the other hand, should be performed at a level at which the lactate removal mechanisms function maximally, i.e. preferably at a stress level just below the anaerobic limit.

An embodiment of the physiological model is shown in FIG. 2B. The person's stress level 208 during exercise is fed into the model as input data. A delay unit 212A enables presentation of the model as a neural network according to an embodiment. Since the physiological model is preferably in the form of a differential equation, a discrete form of the model can be implemented by a delay unit 212 which provides feedback. The physiological model with units 212B to 212D can be expressed simply by formula (1)

$$\frac{d la(t)}{dt} = \frac{1}{V}[Ra(t) - Rd(t)] \quad (1)$$

where la(t) is the lactate concentration, Ra(t) is the lactate production rate, R(d) is the lactate removal rate and V is the lactate breakdown rate. Parameter k in the model represents the dependency of Ra on the stress level 208, represents the dependency of Rd on the stress level, n represents the dependency of Rd on la, and s the dependency of Rd on Rdmax. The above-mentioned parameters of the model may be adapted to their user-specific optimal values on the basis of a reference exercise performed by the user. In the reference exercise the stress parameters are accurately defined.

As output the model provides the lactate amount 214 in the body, which can be fed into a controller 216 monitoring recovery according to FIG. 2A. Instead of the controller 216, a person, i.e. the exerciser or his/her coach, can also control the recovery exercise. The controller 216 preferably monitors that the amount of lactate remains below the threshold value, in which case the lactate removal rate is higher than the lactate production rate. Furthermore, the controller preferably monitors the duration of the recovery exercise, i.e. the fact that a sufficient amount of lactate is removed from the body to avoid stress pain caused by lactate. In a preferred embodiment of the invention the controller 216 also receives information on the heart rate, and, in addition to lactate values, the controller 216 uses the change point of heart rate variation in controlling recovery from a fitness exercise. The control function 218 provided by the controller 216 can be supplied e.g. to the display of the heart rate monitor or provided for the user as a voice message.

FIG. 3B illustrates feeding of user-specific information into the model and adaptation of the model to a certain user. In step 322 user-specific physiological parameters are fed into the mathematical model. The mathematical model, such as a neural network model, and physiological parameters are used for forming a rough estimate of the user's physical condition. In step 324 stress parameters corresponding to a reference exercise are fed into the model. A reference exercise, e.g. a 12-minute running exercise in accordance with the Cooper's test, is performed in step 326. On the basis of the running speed and heart rate, a specified estimate of the user's condition can be formed using the fitness parameters, such as the maximal oxygen uptake.

FIG. 3C illustrates use of a solution implemented by the method of the invention. In step 342 the user's maximum heart rate is calculated by the formula 220-age, and thus the maximum heart rate of a 30-year person, for example, is 190. In step 344 the person's threshold heart rate is calculated, which is 63% of the maximum heart rate, i.e. 120 in this case. The threshold heart rate value is thus a rough estimate of the person's anaerobic limit. According to an embodiment of the invention, the person's condition is used for specifying the threshold heart rate. For example, if 10 beats are added to the threshold heart rate value of a fit person, the person's threshold heart rate will be 130. In step 346 the person carries out the actual fitness exercise the recovery from which is to be controlled according to the invention. The models described in connection with FIGS. 2A to 2B are used for estimating the lactate concentration in the person's body as a function of heart rate. In step 348 the fitness exercise is monitored and finished, after which the person starts a recovery exercise, which, according to the example, should also be performed at a relatively heavy workload, at a heart rate slightly below 130. According to a preferred embodiment, the controller shown in FIG. 2B or the exerciser or another person monitors the amount of lactate during recovery, i.e. the fact that the lactate removal rate is optimal and at least exceeds the production rate. A sufficient duration can be determined for the recovery exercise from the threshold value formed for the amount of lactate in accordance with step 350.

FIG. 4A shows a person 400 who performs an exercise on a treadmill 406. The heart rate of the person 200 is measured by means of a transmitter electrode belt 402 fitted around the chest. The heart rate is measured by two or more electrodes 410A to 410B of the transmitter electrode belt 402, between which a difference of potential is created as the heart beats. The transmitter electrode belt 402 is fitted around the person's chest by means of an elastic band made of elastic material, for instance. The measured heart rate is preferably transmitted inductively to a wrist-worn receiver 404 which preferably also comprises a display for showing the measured heart rate. The invention is also applicable to heart rate monitors, in which the electrode belt 402 on the chest, in addition to measuring, takes care of storing, processing and displaying the heart rate information, and thus the wrist-worn receiver unit 404 is unnecessary. The heart rate monitor can also be a single wrist-worn device, in which the transmitter part and the receiver part are integrated into one single device, and, thus transmitter and receiver electronics are unnecessary. The heart beat can be measured from the wrist, either from an ECG signal, arterial pressure pulse or by observing optically changes in the absorption or reflection of blood circulation.

FIG. 4B shows the electrode belt 402 of FIG. 4A in greater detail. In FIG. 4B, the electrode belt 402 is illustrated from the side of the electrodes 410A to 410B, i.e. from the side facing the body. The figure also shows securing means 416A to 416B, by which the electrode belt 402 can be secured to an elastic band to be fitted around the chest. In FIG. 4B, an electronic unit 412 for processing the heart rate information obtained from the electrodes 410A to 410B is illustrated by a broken line. The electrodes 410A and 410B are connected to the electronic unit 412 with conductors 414A and 414B, respectively.

FIG. 4C illustrates the structures of the transmitter electrode belt 402 and the receiver 404 by means of an embodiment. The topmost part of the figure shows the transmitter electrode belt 402, the middle part shows a sample of heart rate information to be transmitted and the bottom part shows the essential parts of the receiver unit 404. The electronic unit 112 of the transmitter electrode belt 402 receives heart rate information from the means 410A to 410B for measuring one or more heart rate parameters. The measuring means 410A to 410B are preferably electrodes. The heart rate monitor comprises at least two electrodes, but more can also be used. From the electrodes the signal is applied to an ECG preamplifier 420 from which the signal is transferred via an AGC amplifier 422 and a power amplifier 424 to a transmitter 426. The transmitter 426 is preferably implemented as a coil which sends the heart rate information 430 inductively to a receiver, such as a wrist-worn receiver unit 404 or to an external computer, for instance.

One 5 kHz burst 432A corresponds to one heart beat, for instance, or a cluster of a plurality of bursts 432A to 432C may correspond to one beat. The intervals 432A to 432B of bursts 430A to 430C can be equal or different in duration, as appears from FIG. 4C. Information can be transmitted inductively, or alternatively, optically or via a conductor, for instance. In an embodiment, the receiver 404, such as the wrist-worn receiver, comprises a receiver coil 440, from which the received signal is applied through a signal receiver 442 to a central processor 444, which coordinates the operation of different parts. The receiver 404 preferably also comprises a memory 448 for storing the heart rate information and display means 450 for presenting the heart rate or the heart rate parameters derived from it, such as the standard deviation. In a preferred embodiment of the invention the display means 450 also show information needed to control recovery, such as the heart rate level at which the recovery exercise is optimal and the recovery exercise duration. The display means 450 can also show the amount of lactate in the person's body or the person's stress level, for instance. The display means 450 is, for example, the display of a heart rate monitor or a speech controller. In preferred embodiments the display means 450 may also comprise means for transmitting the heart rate and/or feedback information to an external computer or data network. The transmitting means can be implemented e.g. as an induction coil, an optical transmitter, or a connector for transmission via a connecting line. A heart rate measuring arrangement is in question if the information measured or generated by the heart rate monitor is transmitted to equipment outside the heart rate monitor, such as a computer. According to a preferred embodiment, the display means are then located in the computer, by which the information measured in real-time or stored in the memory 448 of the heart rate monitor can be displayed.

The heart rate monitor further comprises forming means 452 for forming control information from the measured heart rate information for controlling the recovery exercise. The forming means 452 are preferably implemented as the heart rate monitor's calculating unit. The calculating unit preferably implements the functions required by the method of the invention for forming control information, such as location of the change point of heart rate variation in one embodiment or calculation of a person's maximum heart rate value on the basis of age. In a preferred embodiment the calculation unit 452 comprises a mathematical model 200, which by means of input parameters provides e.g. the amount of lactate in the body and/or the person's stress level as output parameters. In that case, the calculation unit 452 forms the control information using the output parameters provided by the model. The output parameters provided by the model can naturally be presented as such by the display means 450 of the heart rate monitor. It is clear that the calculating unit 542 need not be implemented as a separate device unit but the calculating unit 452 and the mathematical model 200 included therein can be part of the central processor 444. Further, it is clear that the heart rate monitor need not necessarily comprise a separate calculating unit 452 but the model 200 can be implemented in the central processor 444, for instance. The heart rate monitor, i.e. receiver 404 in the solution of FIG. 4C, preferably comprises feeding means 446, such as a keypad or speech controller means. The feeding means 446 can be used e.g. for feeding the physiological parameters and stress parameters required by the model 200.

In a preferred embodiment of the invention the functions, means and one or more models implementing the method steps of the invention are implemented by means of software in a general-purpose processor. Said means can also be implemented as ASIC, by separate logic components or by any corresponding known method.

In the embodiment of FIG. 4C the heart rate monitor refers to an entity consisting of the transmitter electrode belt 402 and the receiver 404. In an embodiment, the heart rate monitor can also be implemented so that the above-described functions included in the transmitter electrode belt 402 and the receiver 404 are located in one device. This one-piece device can be either fitted on the chest for heart rate measurement, or alternatively, worn on the wrist. It is obvious to a person skilled in the art that the electrode belt 402 and the receiver 404 may also comprise other parts than those shown in FIGS. 4B and 4C, but it is not relevant to describe them here.

Even though the invention has been described by means of examples according to the attached drawings, it is clear that the invention is not limited to them, but may be modified in various ways within the inventive concept defined in the appended claims.

What is claimed is:

1. A method of controlling recovery of a person from a fitness exercise having an exercise workload performed by him/her, comprising:

controlling a recovery exercise following the fitness exercise so that the recovery exercise is performed at a heart rate or at heart rates below a threshold value of the heart rate, wherein the heart has a temporal variation of heart beats and an expected moment at which the heart should beat, and wherein said heart rate variation is the temporal variation in heart beats around the expected moments at which the heart should beat;

wherein said person has a body, a heart, a physical condition and a maximal oxygen uptake, and wherein said body has an amount of lactate and a lactate concentration and said heart has a heart beat having an actual moment or actual moments and an expected moment; wherein the threshold value of the heart rate is below the level at which lactate is formed and corresponds to a heart rate variation of between 3 to 8 ms, and wherein the recovery exercise reduces the amount of lactate in the body.

2. A method according to claim 1, wherein said threshold value of the heart rate is specified by means of a fitness parameter or fitness parameters that represent the physical condition of the person to be measured.

3. A method according to claim 2, wherein the fitness parameter, representing the person's physical condition and used for specifying the threshold value of the heart rate, is the person's maximal oxygen uptake.

4. A method according to claim 2, wherein the person's physical condition needed to specify the threshold value of the heart rate belongs to one or more classes in a fitness classification comprising two or more classes.

5. A method according to claim 4, wherein the fitness classification comprises two or more of the following classes: good, average, poor.

6. A method according to claim 2, wherein the person's physical condition needed to specify the threshold value of the heart rate is estimated by means of a neural network into which one or more of the following parameters are fed as input data: one or more heart rate parameters, a physiological parameter or physiological parameters describing the person's physiology, one or more stress parameters describing the exercise workload.

7. A method according to claim 3, wherein the threshold value of the heart rate is obtained by calculating about 45 to 55% of the heart rate corresponding to the person's maximal oxygen uptake.

8. A method according to claim 1, wherein the threshold value of the heart rate is obtained by calculating about 60 to 70% of the person's maximum heart rate.

9. A method according to claim 8, wherein the maximum heart rate is determined by measuring the heart rate that corresponds to a maximum exercise workload or by estimating it on the basis of the person's age.

10. A method according to claim 1, wherein the heart rate variation is about 3 to 5 ms.

11. A method according to claim 1, wherein the heart rate variation represents a difference between the actual moment of the heart beat and the expected moment of the heart beat calculated from the heart rate.

12. A method according to claim 1, wherein the heart rate variation is formed as a standard deviation from a difference between the actual moment or actual moments of the heart beat and the expected moment of the heart beat calculated from the heart rate.

13. A method according to claim 1, wherein the recovery exercise is controlled based on the lactate concentration in the person's body, wherein said body has a lactate production rate in a muscle or muscles, a lactate removal rate from said muscle or muscles, a blood volume into which said lactate from said muscle or muscles is dispersed and a threshold level of lactate concentration at which the recovery exercise can be finished.

14. A method according to claim 13, wherein the amount of lactate in the person's body is estimated by means of physiological model, which determines the influence of the workload of the fitness exercise performed by the person on the amount of lactate in the person's body.

15. A method according to claim 13, wherein at least the lactate production rate in a muscle, the lactate removal rate from the muscle and the blood volume into which the lactate is dispersed are used for estimating the amount of lactate.

16. A method according to claim 13, wherein the lactate concentration in the body is used for estimating a sufficient duration of the recovery exercise.

17. A method according to claim 13, wherein a sufficient duration of the recovery exercise is estimated by means of the threshold level of lactate concentration at which the recovery exercise can be finished.

18. A method according to claim 13, wherein a physiological model is implemented as a neural network into which at least one or more of the following parameters are fed as input data: a heart rate parameter or heart rate parameters, a physiological parameter or physiological parameters describing the person's physiology, one or more stress parameters describing the exercise workload, one or more fitness parameters describing the person's physical condition, the person's stress level.

19. A method according to claim 6, wherein said physiological parameter is age, weight, height or gender.

20. A method according to claim 6, wherein said stress parameter is running speed or resistance of an exercise bike.

21. A method according to claim 6, wherein said heart rate parameter is the heart rate, heart rate variation, or change rate of the heart rate.

22. A method according to claim 1, wherein the heart rate is measured by a heart rate monitor comprising a display, and wherein information needed for controlling the recovery exercise is formed by means of the heart rate monitor and the information needed to control the recovery exercise is presented on the display of the heart rate monitor.

23. A method according to claim 22, wherein the information needed to control recovery consists of one or more of the following items: heart rate, heart rate limits, recovery time.

24. A heart rate measuring arrangement, comprising:
   measuring means for measuring a heart rate of a person to obtain heart rate information to control a recovery exercise, wherein said person has a maximum heart rate and said heart rate has a heart rate variation, and wherein said heart rate variation is the temporal variation in heart beats around the expected moments at which the heart should beat;
   forming means for forming control information from the heart rate information, wherein the forming means is a calculation unit of a heart rate monitor, and wherein the calculation unit is arranged to locate a change point of the heart rate variation from the heart rate information obtained by measuring and use said change point for forming control information, and
   display means for presenting the formed control information,
   wherein said person has a body, a heart, a physiology, a physical condition and a maximal oxygen uptake, wherein said body has an amount of lactate, a lactate concentration, a lactate production rate in a muscle or muscles, a lactate removal rate from the muscle or muscles, a blood volume into which the lactate from the muscle or muscles is dispersed and a threshold level of the lactate concentration at which the recovery exercise can be finished, wherein the heart has a heart beat having an actual moment or actual moments and an expected moment, wherein the calculation unit is arranged to control the recovery exercise so that it is performed at a heart rate or at heart rates below a threshold value of the heart rate, wherein the threshold value of the heart rate is below the level at which lactate is formed and corresponds to a heart rate variation of between 3 to 8 ms, and wherein the recovery exercise reduces the amount of lactate in the body.

25. A heart rate measuring arrangement according to claim 24, wherein the control information comprises a duration of the recovery exercise.

26. A heart rate measuring arrangement according to claim 24, wherein the heart rate measuring arrangement comprises a memory for storing the heart rate information.

27. A heart rate measuring arrangement according to claim 24, wherein the measuring means comprise an electrode belt for measuring the heart rate, the heart rate measuring arrangement further comprising a receiver unit, which comprises forming means and display means.

28. A heart rate measuring arrangement according to claim 27, wherein the display means is the display of the receiver unit.

29. A heart rate measuring arrangement according to claim 24, wherein the heart rate measuring arrangement is a one-piece wrist-worn heart rate monitor.

30. A heart rate measuring arrangement according to claim 24, wherein the calculation unit is arranged to calculate that the threshold value of the heart rate is 45 to 55% of the heart rate corresponding to the person's maximal oxygen uptake.

31. A heart rate measuring arrangement according to claim 24, wherein the calculation unit is arranged to calculate that the threshold value of the heart rate is 60 to 70% of the person's maximum heart rate.

32. A heart rate measuring arrangement according to claim 31, wherein the calculation unit is arranged to use the heart rate corresponding to a maximum exercise workload as the maximum heart rate or the heart rate estimated based on the person's age.

33. A heart rate measuring arrangement according to claim 24, wherein the calculation unit is arranged to use about 4 ms as the predetermined threshold value of the heart rate variation.

34. A heart rate measuring arrangement according to claim 24, wherein the heart rate variation describes a difference between the actual moment of the heart beat and the expected moment of the heart beat that can be calculated from the heart rate.

35. A heart rate measuring arrangement according to claim 24, wherein the calculation unit is arranged to form heart rate variation as a standard deviation from a difference between the actual moment or actual moments of the heart beat and the expected moment of the heart beat that can be calculated from the heart rate.

36. A heart rate measuring arrangement according to claim 24, wherein the calculation unit comprises a mathematical model which is arranged to provide an output parameter value or output parameter values for forming the control information in the calculation unit in response to the value of one or more input parameters.

37. A heart rate measuring arrangement according to claim 36, wherein the model is arranged to receive a heart rate parameter or heart rate parameters as its input parameter or input parameters and provide the amount of lactate in the body as the output parameter value.

38. A heart rate measuring arrangement according to claim 37, wherein the model is arranged to use one or more fitness parameters that describe the person's physical condition for estimating the amount of lactate.

39. A heart rate measuring arrangement according to claim 38, wherein the fitness parameter is the person's maximal oxygen uptake.

40. A heart rate measuring arrangement according to claim 36, wherein the mathematical model is arranged to receive one or more of the following parameters as input data: one or more physiological parameters describing the person's physiology, one or more stress parameters describing an exercise workload.

41. A heart rate measuring arrangement according to claim 36, wherein the mathematical model is arranged to estimate the amount of lactate in the person's body on the basis of a stress level experienced by the person during the fitness exercise.

42. A heart rate measuring arrangement according to claim 36, wherein the mathematical model is arranged to estimate the amount of lactate in the person's body by means of one or more of the following items: the lactate production rate in a muscle, the lactate removal rate in the muscle and the blood volume into which the lactate is dispersed.

43. A heart rate measuring arrangement according to claim 24, wherein the calculation unit is arranged to use the lactate concentration in the body in forming of control information for the recovery exercise.

44. A heart rate measuring arrangement according to claim 24, wherein the calculation unit is arranged to estimate a sufficient duration for the recovery exercise by means of the threshold level of the lactate concentration at which the recovery exercise can be finished.

45. A heart rate measuring arrangement according to claim 36, wherein the mathematical model is a neural network.

46. A heart rate measuring arrangement according to claim 45, wherein the neural network is trained on the basis of user information collected from a large number of users.

47. A heart rate measuring arrangement according to claim 45, wherein weighting coefficients between neurons used in the training of the neural network have been specified by means of feedback utilizing the output parameter value or the output parameter values.

48. A heart rate measuring arrangement according to claim 40, wherein said physiological parameter is age, weight, height or gender.

49. A heart rate measuring arrangement according to claim 40, wherein said stress parameter is running speed or resistance of an exercise bike.

50. A heart rate measuring arrangement according to claim 37, wherein said heart rate parameter is the heart rate, the heart rate variation or the change rate of the heart rate.

51. A method according to claim 18, wherein said physiological parameter is age, weight, height or gender.

52. A method according to claim 18, wherein said stress parameter is running speed or resistance of an exercise bike.

53. A method according to claim 18, wherein said heart rate parameter is the heart rate, the heart rate variation or change rate of the heart rate.

* * * * *

UNITED STATES PATENT AND TRADEMARK OFFICE
CERTIFICATE OF CORRECTION

PATENT NO. : 6,687,535 B2
DATED : February 3, 2004
INVENTOR(S) : Hautala et al.

It is certified that error appears in the above-identified patent and that said Letters Patent is hereby corrected as shown below:

<u>Title page,</u>
Item [74], *Attorney, Agent or Firm,* now reads "Hoffman & Baron, LLP" should read
-- Hoffmann & Baron, LLP --

<u>Column 8,</u>
Line 25, reads "the dependency of Ra on the stress level 208, represents the" should read -- the dependency of Ra on the stress level 208, l represents the --

Signed and Sealed this

Eighth Day of June, 2004

JON W. DUDAS
*Acting Director of the United States Patent and Trademark Office*